US010933205B2

(12) United States Patent
Lefkowitz

(10) Patent No.: US 10,933,205 B2
(45) Date of Patent: Mar. 2, 2021

(54) PORTABLE HEATED MIST INHALER

(71) Applicant: Aura Medical LLC, Brooklyn, NY (US)

(72) Inventor: Chana Lefkowitz, Brooklyn, NY (US)

(73) Assignee: Aura Medical LLC, Brooklyn, NY (US)

( * ) Notice: Subject to any disclaimer, the term of this patent is extended or adjusted under 35 U.S.C. 154(b) by 299 days.

(21) Appl. No.: 16/177,495

(22) Filed: Nov. 1, 2018

(65) Prior Publication Data

US 2019/0160234 A1 May 30, 2019

Related U.S. Application Data

(60) Provisional application No. 62/592,525, filed on Nov. 30, 2017.

(51) Int. Cl.

| | |
|---|---|
| ***A61M 11/04*** | (2006.01) |
| ***A61M 15/00*** | (2006.01) |
| ***A61M 15/08*** | (2006.01) |
| ***A61M 16/10*** | (2006.01) |
| ***B05B 1/24*** | (2006.01) |
| *B05B 17/06* | (2006.01) |

(Continued)

(52) U.S. Cl.

CPC ...... *A61M 11/041* (2013.01); *A61M 15/0086* (2013.01); *A61M 15/08* (2013.01); *A61M 16/1075* (2013.01); *B05B 1/24* (2013.01); *A61M 2205/3368* (2013.01); *B05B 7/0425* (2013.01); *B05B 17/0607* (2013.01); *B05B 17/0646* (2013.01)

(58) Field of Classification Search

CPC ....... B05B 1/24; B05B 11/0002; B05B 7/164; A61M 11/00; A61M 11/005; A61M 11/041; A61M 11/042; A61M 13/00; A61M 15/00; A61M 15/0085; A61M 15/08; A61M 16/1075; A61M 2205/3368; A61M 35/00; A61M 35/003; A61M 35/30; A61H 35/04

See application file for complete search history.

(56) References Cited

U.S. PATENT DOCUMENTS 6,196,218 B1 * 3/2001 Voges .................. A24F 47/002 128/200.14
6,651,650 B1 11/2003 Yamamoto et al.

(Continued)

FOREIGN PATENT DOCUMENTS

CN 206414769 U 8/2017
CN 207804728 U 9/2018

OTHER PUBLICATIONS

English translation of "Portable warm inhaler of low temperature formula of taking" application CN207804728 U published Sep. 4, 2018.

(Continued)

*Primary Examiner* — Joseph D. Boecker
(74) *Attorney, Agent, or Firm* — Mark Nowotarski

(57) ABSTRACT

A portable heated mist inhaler has a body, a supply tank of liquid, an atomizer for atomizing the liquid, and a thermostatically controlled heated nozzle. The supply tank feeds liquid to the atomizer. The atomizer creates a stream of mist from the liquid and entrained surrounding air. The mist is heated inside the nozzle so that it will be comfortable for the user. The portable heated mist inhaler has a battery which powers the atomizer and the heated nozzle.

5 Claims, 5 Drawing Sheets

(51) Int. Cl.

| | |
|---|---|
| *B05B 7/04* | (2006.01) |
| *B05B 17/00* | (2006.01) |

(56) References Cited

U.S. PATENT DOCUMENTS

| | | | |
|---|---|---|---|
| 7,920,777 | B2 | 4/2011 | Rabin et al. |
| 2005/0016550 | A1 * | 1/2005 | Katase .................. A24F 47/008 131/194 |
| 2005/0067503 | A1 * | 3/2005 | Katase .................. A24F 47/002 239/373 |
| 2008/0271732 | A1 * | 11/2008 | Weaver ............. A61M 15/0066 128/200.14 |
| 2010/0319685 | A1 | 12/2010 | Yu |
| 2019/0184701 | A1 * | 6/2019 | Jeute ........................ B41J 2/105 |
| 2019/0351155 | A1 | 11/2019 | Montagnino et al. |

OTHER PUBLICATIONS

Avya—The Battery-Powered Steam Inhaler by Aura Medical on Kickstarter, https://www.kickstarter.com/projects/1739461510/avya-the-battery-powered-steam-inhaler-by-aura-med, last viewed Dec. 17, 2019.

English translation of CN206414769 U published Aug. 18, 2017 for Quatek Holding.

The Aura Portable Atomizer, https://web.archive.org/web/20160807015100/http://www.aura-medical.com:80/products, dated Aug. 7, 2016.

* cited by examiner

PORTABLE HEATED MIST INHALER

COPYRIGHT AND TRADEMARK NOTICE

A portion of the disclosure of this patent document contains material to which a claim for copyright is made. The copyright owner has no objection to the facsimile reproduction by anyone of the patent document or the patent disclosure, as it appears in the Patent and Trademark Office patent file or records, but reserves all other copyright rights whatsoever.

FIELD OF THE INVENTION

Embodiments of the present invention relate to mist inhalers.

BACKGROUND OF THE INVENTION

FIG. 1 is a photograph of prior art ambient mist inhaler 100. The mist inhaler is battery operated portable mist inhaler made by Aura Medical LLC. The mist inhaler comprises a supply tank 102 disposed above an atomizer 104. The atomizer can be any device for generating a fine mist from a liquid in the supply tank. A suitable atomizing device is a vibrating mesh technology. A suitable vibrating mesh technology is described in U.S. patent application US2010/0319685 A1, "Medical Liquid Droplet Apparatus" by Neng-Chih Yu, Dec. 23, 2010. Said patent application is incorporated herein by reference with specific reference to FIG. 4. The mist inhaler comprises a body 108 below the supply tank. The body comprises an on/off switch 112. Batteries (not shown) are provided in the body to power the vibrating mesh. A nozzle 106 is disposed in front of the vibrating mesh. In operation, a liquid in the supply tank flows down to the atomizer. The atomizer is adapted to eject the liquid in an atomized state into the nozzle. The atomized liquid entrains air to form a mist that the user inhales. The liquid can be water or any other liquid suitable for inhalation by a user.

One of the drawbacks of the prior art is that, as the atomized liquid mixes with the ambient air, a portion of it evaporates thus causing a drop in the temperature of the mist. This can cause discomfort, particularly when the ambient air is very dry with a low dewpoint or frost point. Experiment has shown that heating the liquid before atomizing does not help increase the temperature of the mist. There is need, therefore, for a hand-held battery operating mist inhaler that can deliver a warm mist for user comfort.

SUMMARY OF THE INVENTION

The summary of the invention is provided as a guide to understanding the invention. It does not necessarily describe the most generic embodiment of the invention or the broadest range of alternative embodiments.

FIG. 2 is a perspective drawing of a portable heated mist inhaler 200. The portable heated mist inhaler comprises a supply tank 202 for liquid, an atomizer 204 (inside the body) for generating atomized liquid and a body 208 that can be used to hold the portable heated mist inhaler. The body may also house a battery power supply and associated electronics. A heated nozzle 206 proceeds from the front of the portable heated mist inhaler. The heated nozzle comprises an inlet orifice (item 324 FIG. 3) located at a nozzle inlet (item 334 FIG. 3), a thermostatically controlled heating element (item 322 FIG. 3) located inside of the heated nozzle, an outlet orifice 220 located at a nozzle outlet 224, and an air orifice 210 located at a nozzle base 222. The nozzle base is the portion of the nozzle adjoining the inhaler face 223. The body further comprises an on/off switch 212, a variable temperature switch 214, 218 and a temperature indicator 216.

In operation, fluid flows from the supply tank to the atomizer. The atomizer creates a stream of atomized fluid that flows into the inlet of the heated nozzle. The stream of atomized fluid entrains air through the air orifice to form a mist. The mist passes over the thermostatically controlled heating element where its temperature is raised to the temperature set by the variable temperature switch. The heated mist then proceeds out through the outlet orifice where it is then inhaled by a user. The temperature can be increased by activating the upper variable temperature switch 214. The temperature can be decreased by activating the lower variable temperature switch 218. Any control means, however, may be used. The setpoint temperature is indicated by the temperature indicator. The temperature indicator may simply be a series of lights where more lights indicate a higher set point. Any indicator means, however, may be used.

DETAILED DESCRIPTION

The detailed description describes non-limiting exemplary embodiments. Any individual features may be combined with other features as required by different applications for at least the benefits described herein. As used herein, the term "about" means plus or minus 10% of a given value unless specifically indicated otherwise.

As used herein, the term "shaped" means that an item has the overall appearance of a given shape even if there are minor variations from the pure form of said given shape.

As used herein, the term "generally" when referring to a shape means that an ordinary observer will perceive that an object has said shape even if there are minor variations from said shape.

As used herein, relative orientation terms, such as "up", "down", "top", "bottom", "left", "right", "vertical", "horizontal", "distal" and "proximal" are defined with respect to an initial presentation of an object and will continue to refer to the same portion of an object even if the object is subsequently presented with an alternative orientation, unless otherwise noted.

Figure 1:
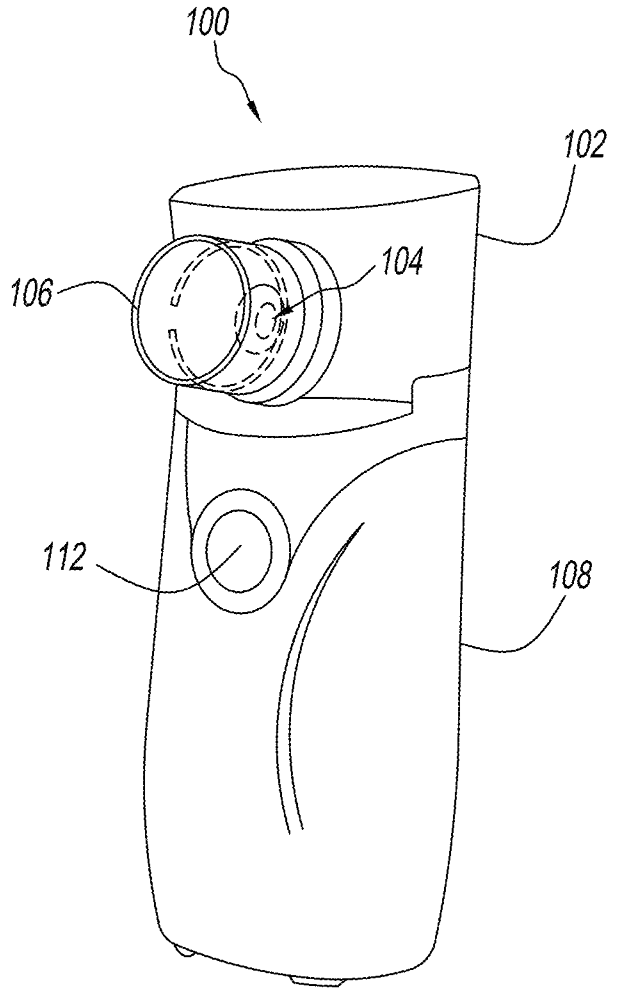
FIG. 1 is a drawing of a prior art ambient mist inhaler.
Figure 2:
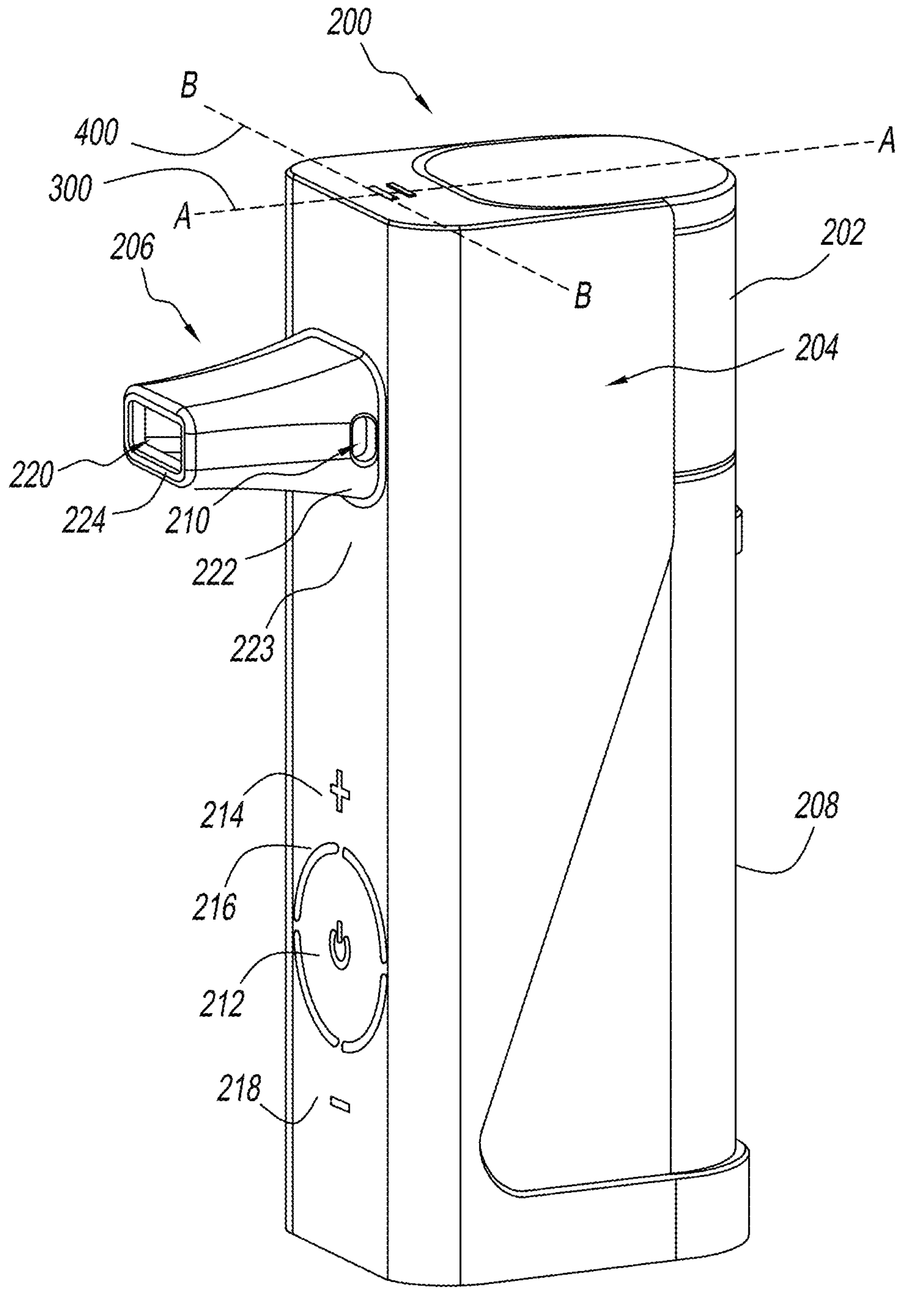
FIG. 2 is a perspective drawing of a portable heated mist inhaler.
Figure 3:
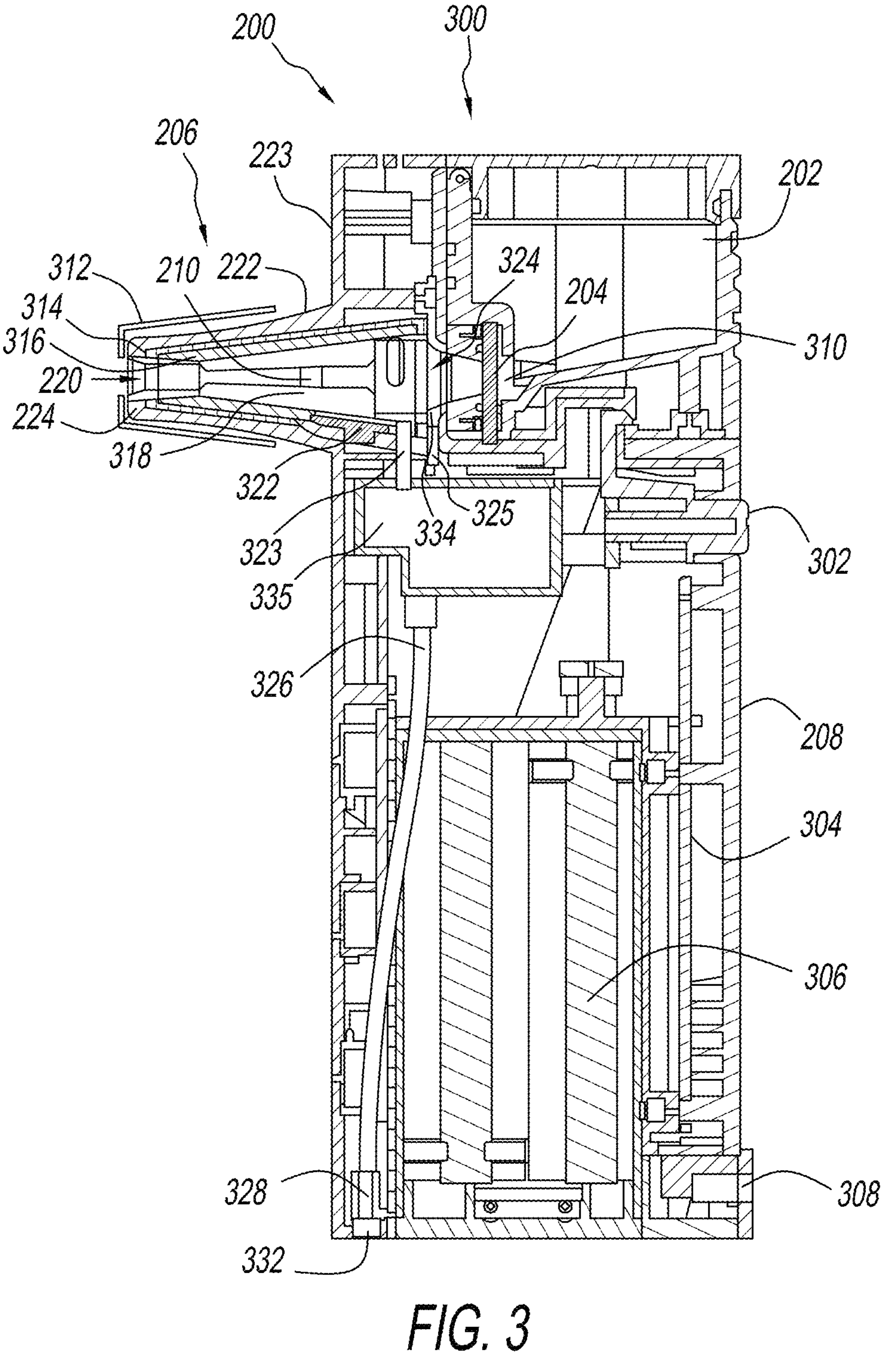
FIG. 3 is a longitudinal cross section drawing of the portable heated mist inhaler of FIG. 2 through section A-A.

FIG. 3 is a longitudinal cross section drawing 300 of the portable heated mist inhaler 200 of FIG. 2 through section A-A. The portable heated mist inhaler comprises:

a) a body 208;

b) a supply tank 202 for holding a liquid to be atomized;

c) an atomizer 204 for atomizing said liquid; and d) a heated nozzle 206 comprising:

i) an inlet 334;

ii) an outlet 224;

iii) a base 222 proximate to said inlet;
iv) an inlet orifice 324 located at said inlet of said nozzle;
v) an outlet orifice 220 located at said outlet of said nozzle;
vi) an air orifice 210 located at said base of said nozzle; and
vii) a thermostatically controlled heating element 322 located at said base of said nozzle wherein:

e) said supply tank is adapted to convey said liquid to said atomizer;
f) said atomizer is adapted to eject said liquid in an atomized state through said inlet orifice;
g) said air orifice is adapted to allow ambient air to mix with said ejected atomized liquid to form a mist which flows out of said outlet orifice;
h) said thermostatically controlled heating element is adapted to heat said flowing mist to a preset temperature; and
i) said preset temperature is a temperature safe for inhalation.

The nozzle may further comprise a heat sink 316. The heat sink may be made of a thermally conductive material, such as a metal alloy, such as an alloy of aluminum or copper. The heat sink may comprise one or more internal fins 318 adapted to contact said mist as said mist flows through said nozzle. The heating element may be in thermal contact with said heat sink such that heat is conducted to said internal fins and hence into the mist. This helps insure a uniform temperature of the mist. A temperature sensor 325 may be provided at the inlet to the nozzle to control the heating element.

The portable heated mist inhaler may further comprise:

a) an accumulator tank 335;
b) a nozzle drain tube 323 connecting said base of said nozzle to said accumulator tank such that fluid that condenses from said mist onto said vertical fins can flow down and drain into said accumulator tank;
c) a drain port 328 at about the bottom of said body;
d) an accumulator drain tube 326 adapted to convey fluid in said accumulator tank to said drain port; and
e) a drain plug 332 adapted to:
 i) prevent said fluid in said accumulator tank from flowing out of said drain port when said drain plug is in place on said drain port; and
 ii) allow said fluid in said accumulator tank to flow out of said drain port when said drain plug is removed from said drain port.

The portable heated mist inhaler may further comprise:

a) a rechargeable battery 306;
b) a control and power circuit 304;
c) a variable temperature switch (collectively items 214, 218 of FIG. 2); and
d) a charging port 308 wherein:

e) said variable temperature switch is adapted to receive input from a user to vary said preset temperature; and
f) said charging port is adapted to connect an external power supply to said rechargeable battery in order to recharge said rechargeable battery.

The portable heated mist inhaler may have a set point that is limited to a temperature for safe inhalation of the mist. Said set point may be in the range of 103° F. to 122° F. The control and power circuit 304 may be adapted to limit said preset temperature to a range of 103° F. to 122° F.

A removable disposable sheath 312 or other attachment or extension may be provided on the outside of the heated nozzle for sanitary, user comfort, or other purposes. An insulating gasket 314 may be provided around the heat sink to insulate the outside of the nozzle from the heat sink. The insulating gasket may be made of an elastomer, such as rubber. A tank release button 302 may be provided to allow easy removal and cleaning of the supply tank. A sump 310 may be provided in the bottom of the supply tank and proximate to the atomizer to allow the atomizer to get full contact with liquid in the supply tank even when the supply tank is almost empty and/or when the portable heated mist inhaler is tilted.

Figure 4:
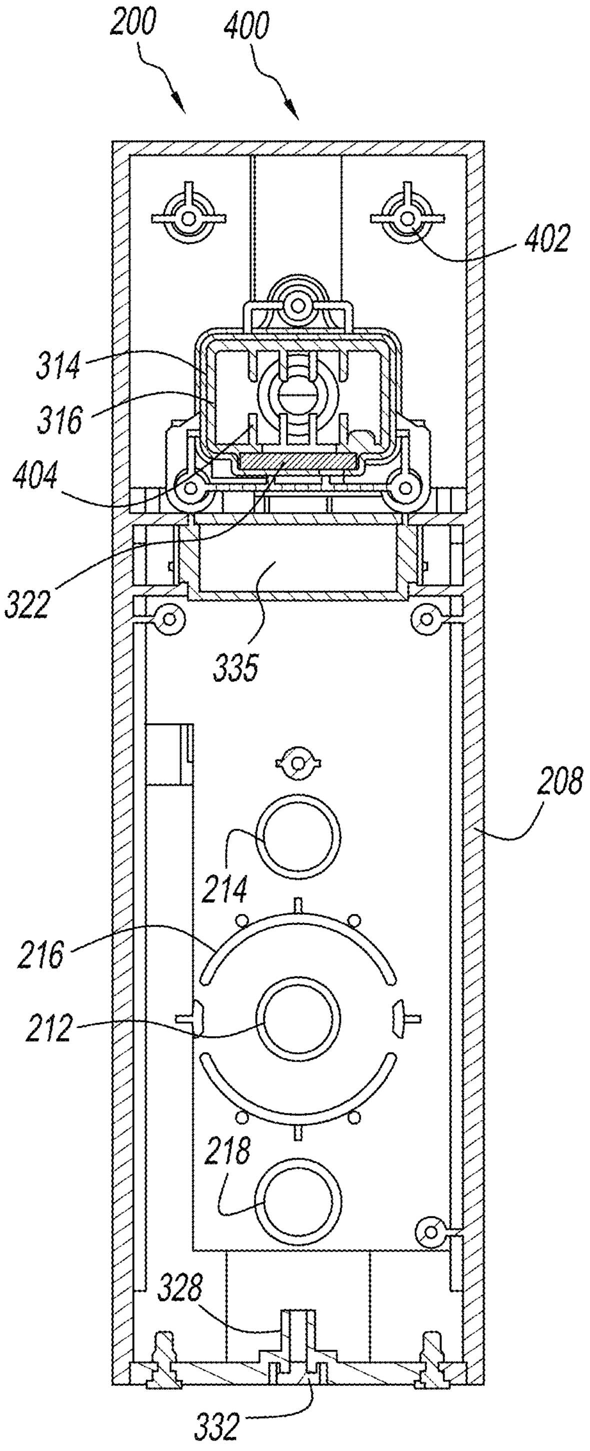
FIG. 4 is a lateral cross section drawing of the portable heated mist inhaler of FIG. 2 through section B-B.

FIG. 4 is a lateral cross section drawing 400 of the portable heated mist inhaler of FIG. 2 through section B-B. Different elements of the portable heated mist inhaler are shown. A plurality of vertical equally spaced internal fins 404 can be seen. The cross section of various screw mounts 402 can be seen. The drain tube 326 is not shown on the drain port 328 for clarity.

Figure 5:
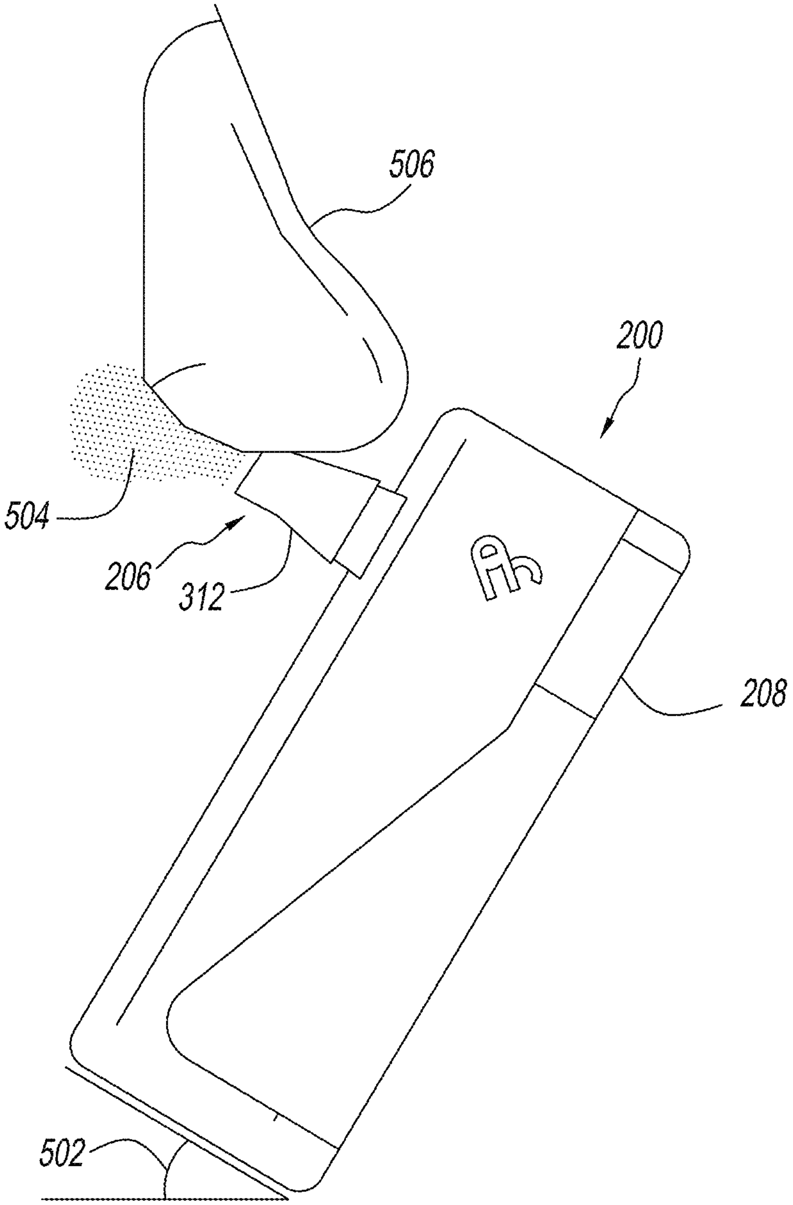
FIG. 5 is a drawing of a user using the portable heated mist inhaler of FIG. 2.

FIG. 5 is a drawing of a user using the portable heated mist inhaler 200 of FIG. 2. The user tips the body 208 back at a tipping angle 502 so that warmed mist 504 will emerge from the heated nozzle directly into the user's nose 506. The insulating gasket (314 FIG. 3) keeps the user's nose from getting heated. The removable disposable sheath 312 keeps the heated nozzle sanitary.

CONCLUSION

While the disclosure has been described with reference to one or more different exemplary embodiments, it will be understood by those skilled in the art that various changes may be made and equivalents may be substituted for elements thereof without departing from the scope of the disclosure. In addition, many modifications may be made to adapt to a particular situation without departing from the essential scope or teachings thereof. Therefore, it is intended that the disclosure not be limited to the particular embodiment disclosed as the best mode contemplated for carrying out this invention.

I claim:

1. A portable heated mist inhaler comprising:

a) a body;
b) a supply tank for holding a liquid to be atomized;
c) an atomizer for atomizing said liquid; and
d) a heated nozzle comprising:
 i) an inlet;
 ii) an outlet;
 iii) a base proximate to said inlet;
 iv) an inlet orifice located at said inlet of said nozzle;
 v) an outlet orifice located at said outlet of said nozzle;
 vi) an air orifice located at said base of said nozzle; and
 vii) a thermostatically controlled heating element located at said base of said nozzle wherein:

e) said supply tank is adapted to convey said liquid to said atomizer;
f) said atomizer is adapted to eject said liquid in an atomized state through said inlet orifice;
g) said air orifice is adapted to allow ambient air to mix with said ejected atomized liquid to form a mist which flows out of said outlet orifice;
h) said thermostatically controlled heating element is adapted to heat said flowing mist to a preset temperature; and
i) said preset temperature is a temperature safe for inhalation.

2. The portable heated mist inhaler of claim 1 wherein:
a) said nozzle further comprises a heat sink;
b) said heat sink comprises a plurality of internal fins adapted to contact said mist as said mist flows through said nozzle; and
c) said heating element contacts said heat sink such that heat is conducted to said internal fins.

3. The portable heated mist inhaler of claim 2 which further comprises:
a) an accumulator tank;
b) a nozzle drain tube connecting said base of said nozzle to said accumulator tank such that fluid that condenses from said mist onto said vertical fins can flow down and drain into said accumulator tank;
c) a drain port at about a bottom of said body;
d) an accumulator drain tube adapted to convey fluid in said accumulator tank to said drain port; and
e) a drain plug adapted to:
i) prevent said fluid in said accumulator tank from flowing out of said drain port when said drain plug is in place on said drain port; and
ii) allow said fluid in said accumulator tank to flow out of said drain port when said drain plug is removed from said drain port.

4. The portable heated mist inhaler of claim 1 which further comprises:
a) a rechargeable battery;
b) a control and power circuit;
c) a variable temperature switch; and
d) a charging port
wherein:
e) said variable temperature switch is adapted to receive input from a user to vary said preset temperature; and
f) said charging port is adapted to connect an external power supply to said rechargeable battery in order to recharge said rechargeable battery.

5. The portable heated mist inhaler of claim 4 wherein said control and power circuit is adapted to limit said preset temperature to a range of 103° F. to 122° F.

* * * * *